United States Patent [19]

Kamen

[11] Patent Number: 4,620,690
[45] Date of Patent: Nov. 4, 1986

[54] MODULAR FLOW CONTROL CASSETTE

[75] Inventor: Dean L. Kamen, Bedford, N.H.

[73] Assignee: Baxter Travenol Laboratories, Inc., Deerfield, Ill.

[21] Appl. No.: 479,328

[22] Filed: Mar. 28, 1983

Related U.S. Application Data

[63] Continuation-in-part of Ser. No. 336,068, Dec. 31, 1981, Pat. No. 4,410,164.

[51] Int. Cl.⁴ ............................................. F14L 55/14
[52] U.S. Cl. ........................................ 251/8; 251/10; 251/7
[58] Field of Search .............................. 251/7, 8, 9, 10

[56] References Cited

U.S. PATENT DOCUMENTS

| | | | |
|---|---|---|---|
| 2,902,248 | 9/1959 | Barton et al. | 251/9 |
| 2,935,088 | 5/1960 | Thompson et al. | 251/9 |
| 3,167,299 | 1/1965 | Ling | 251/8 |
| 3,497,175 | 2/1970 | Koland | 251/9 |
| 3,612,474 | 10/1971 | Strohl | 251/9 |
| 3,724,818 | 4/1973 | Roger | 251/9 |
| 4,265,425 | 5/1981 | Morin | 251/9 |

FOREIGN PATENT DOCUMENTS

| | | | |
|---|---|---|---|
| 2387396 | 12/1978 | France | 251/7 |
| 2079410 | 1/1982 | United Kingdom | 251/10 |

Primary Examiner—William E. Lyddane
Assistant Examiner—Gerald A. Anderson
Attorney, Agent, or Firm—Bromberg, Sunstein & McGregor

[57] ABSTRACT

A sheet with inlet and outlet ports forms a housing, with a flow tube disposed between the ports. In a preferred embodiment, a plurality of arms affixed at one end to the housing are adjustably spaced by a threaded tapered nut which mates with the other end of the arms. The flow tube passes between the arms and is constricted by the arms as the nut is advanced. The thread pitch, the degree of taper, and the point where the tube crosses the arms all determine the rate of constriction. In a further preferred embodiment the tube passes through a transverse indentation in the arms and is bonded thereto. In another preferred embodiment the housing is adapted to removably mount on an automatic flow sensing and adjusting module, which engages the tapered nut to adjust the flow rate through the tube.

20 Claims, 8 Drawing Figures

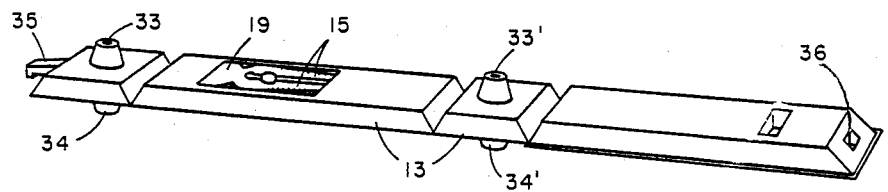
Fig. 3
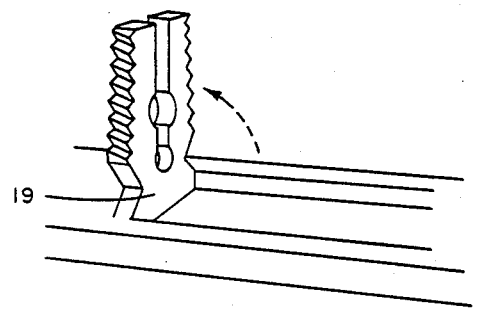
Fig. 3A
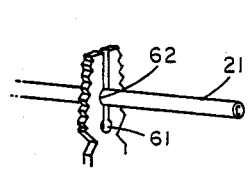 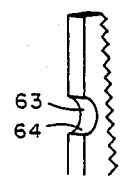
Fig. 6A     Fig. 6B

MODULAR FLOW CONTROL CASSETTE

This application is a continuation-in-part of my co-pending application Ser. No. 336,068, filed Dec. 31, 1981, now U.S. Pat. No. 4,410,164.

TECHNICAL FIELD

This invention relates to medical infusion valves for controlling the rate of flow of a fluid through a tube by constriction of the tube's exterior, and to such valves for use with automatic flow rate sensing and controlling means.

BACKGROUND OF THE INVENTION

A broad variety of medical infusion valves are known in the prior art. Typically such valves operate by clamping down on the exerior surface of an infusion tube, thereby partially constricting the flow path. Such devices are generally used in conjunction with a drip chamber, allowing visual monitoring of the actual rate of flow. Prior art devices of this general type are disclosed in U.S. Pats. Nos. 2,908,476 and 3,960,149. While such a clamp has the advantage of low cost and simplicity of operation, the use of a tube clamp to regulate flow is complicated by the fact that constriction of a tube results in cold flow of the displaced tube wall and consequent changes in the flow path shape and flow rate over the minutes or hours following clamp adjustment. In use, hospital personnel must therefore periodically monitor such flow valves and re-set the valve to account for the flow rate "drift". Such drive may amount to as much as 50% of the selected flow rate over an interval of 20 minutes or less. An additional limitation of such clamps is that tubing, once clamped, does not assume its original shape upon release. This lack of "memory" has as a consequence that when a tube is initially overclamped one cannot simply release the clamp and reset it to a proper value. Instead irregular flow rates will persist for some time as the tubing slowly deconstricts toward its initial shape. Each of these factors requires frequent monitoring and adjustment to attain an acceptable degree of precision in flow rate, thus placing demands upon hospital personnel. These demands can be reduced by using an automated flow adjusting device, such as the device of U.S. Pat. No. 4,137,940; however such a device is significantly more expensive than a simple plastic flow clamp. A problem thus exists as to how to construct a simple flow clamp capable of being manually set to a stable flow rate and requiring minimal human monitoring. A problem also exists as to how to construct such a flow clamp adaptable to, but not requiring, automatic control means and having the structural simplicity and ease of operation of a conventional manually operated valve.

BRIEF DESCRIPTION OF THE INVENTION

The present invention solves the foregoing problems by providing in one embodiment a sheet having an inlet and an outlet port, forming a housing for a flow tube. Attached to the housing is a clamping member having two arms between which the flow tube passes. One end of the pair of arms has the profile of a truncated cone of small taper which is externally threaded, so that turning a nut threaded about the pair of arms progressively constricts the flow tube at a controllable rate. The fineness of the screw threads and the degree of taper of the threaded surface may be so chosen that a full rotation of the nut causes a very small adjustment in flow rate. In one embodiment the arms contain a transverse portion forming a collet surrounding the flow tube and cemented to it for positively deconstricting the flow tube upon release or opening of the valve. In another embodiment the clamp forms an assembly which can be attached to a flow or weight sensing and control mechanism without interrupting or altering the flow setting. These and other features of the invention will become apparent by reference to the drawings.

BRIEF DESCRIPTION OF THE DRAWINGS

FIG. 3 shows an embodiment of the modular cassette, without nut or tubing, before assembly.

FIG. 3A shows the arm assembly raised up in operating position.

FIG. 6A shows a collet embodiment of the clamping arms.

FIG. 6B shows the collet face of one embodiment.

DETAILED DESCRIPTION OF THE INVENTION

Figure 1:
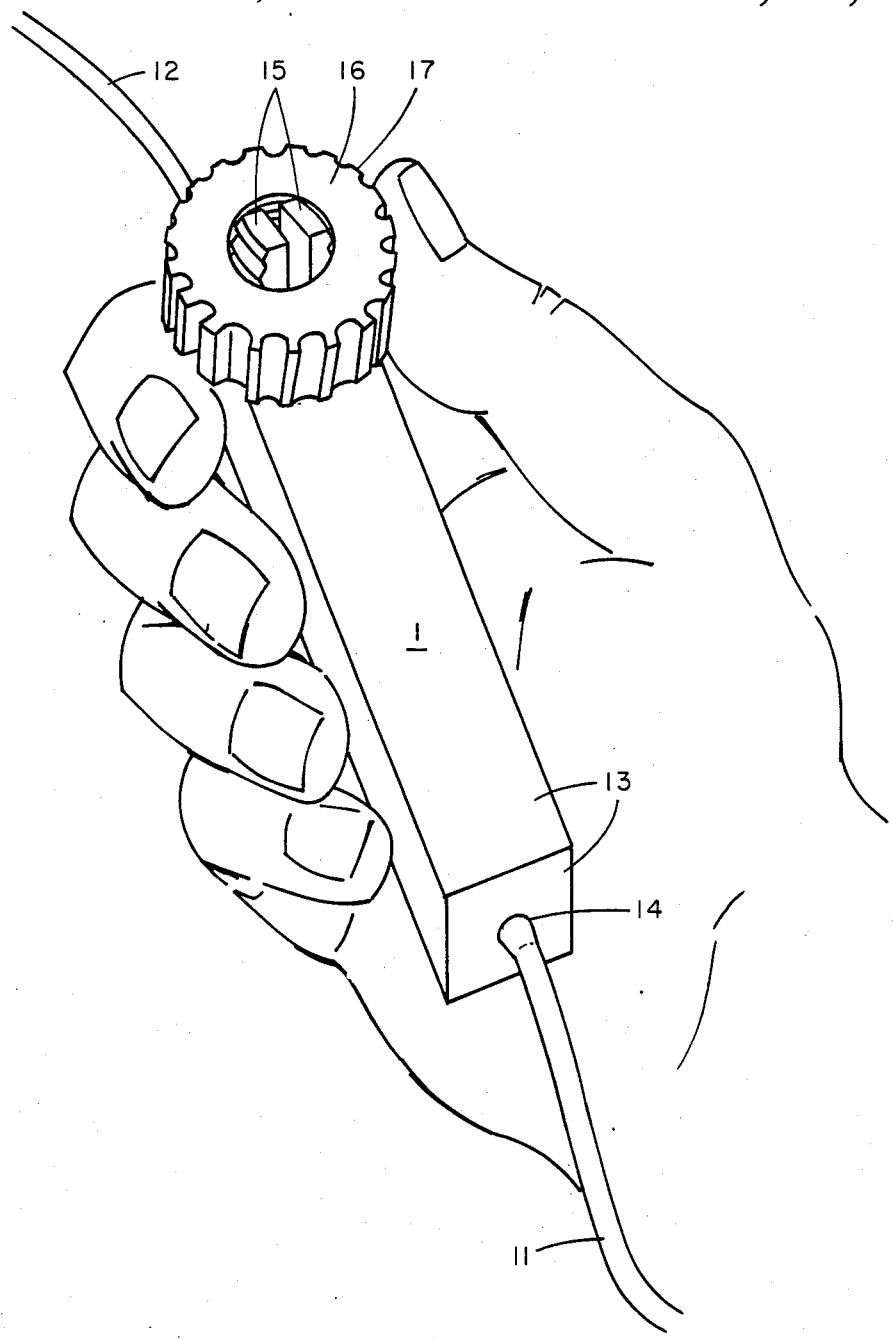
FIG. 1 shows a modular flow control cassette according to the present invention.

FIG. 1 shows one embodiment of a modular flow control cassette 1 according to the present invention, with attached inlet tube 12 and outlet tube 11 of conventional type. The cassette 1 includes a sheet or surface 13 defining a housing. A flow tube (shown at 21 in FIG. 2) passes within the housing connecting the inlet tubing 12 to the outlet tubing 14 and defining a single continuous flow path. The flow tube 21 passes between a pair of arms 15 and is pinched by turning the adjusting nut 16. The inlet and outlet tubes are slideably attached to separate inlet and outlet nipples, similar to nipple 14, as is more clearly shown in FIG. 4 at 34. The use of an internal flow tube of fixed length and free from any load or tensional stress eliminates the variations in flow which might otherwise be caused by such factors.

Figure 2:
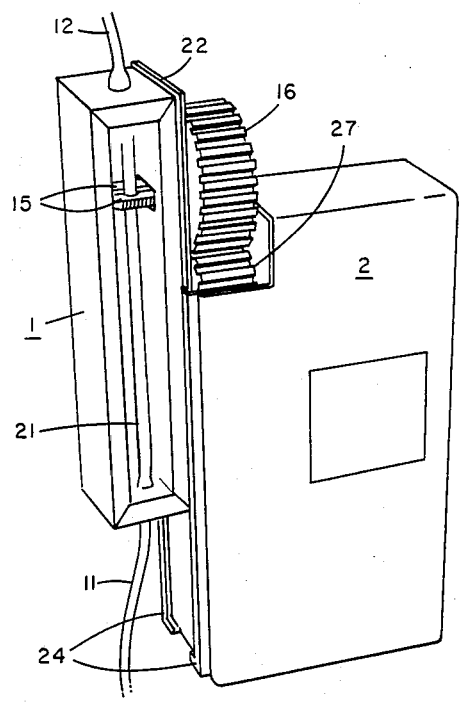
FIG. 2 shows such a clamp inserted into a sensing and control unit.

FIG. 2 shows the modular flow control cassette 1 of FIG. 1 mounted on a control module 2. As shown in FIG. 2 a pair of rails 24 is so positioned that the base 22 of cassette 1 slideably mounts between the rails 24 and is held firmly thereby to the module 2. The cassette 1 slides into the mounting so that the teeth 17 (shown in FIG. 1) of adjusting nut 16 engage corresponding teeth of drive gear 27 of the control module. The control module drive gear 27 rotates to turn the adjusting nut 16 thereby controlling the flow rate. The control module itself may be of any type to effect particular results. Thus it may be a simple device triggering by a weight indicating signal to constrict the cassette valve when an infusion bottle nears a condition of emptiness. It may include a simple drop counter and comparator device which alters the cassette adjustment to maintain a prescribed drop count rate. Or it may include a more sophisticated drop counter with sensors and circuitry to correct the flow rate based on actual total fluid delivery such as the device shown in my pending U.S. patent application Ser. No. 254,304. The control module itself is not a part of this invention and accordingly no further description of it will be given here.

FIG. 3 shows a portion of one embodiment of the cassette, manufactured from a single sheet of plastic in which the faces 13 ultimately comprising the housing surface all lie on one side of the sheet before its assembly by folding into a finished cassette. Clearly visible in FIG. 3 are the two nipples 34, 34' for connection of the inlet and outlet tubes as well as the corresponding two nipples 33, 33' communicating with 34, 34' for connection of the flow tube 21. In this embodiment the pair of arms 15 are part of a fork member 19, shown folded down in the plane of the plastic sheet. Also shown is cutout 36 for accommodating a latch 35.

FIG. 3A is an enlarged detail of fork 19, showing the fork folded up into a normal position for operation, with its two arms 15 perpendicular to the base sheet.

Figure 4:
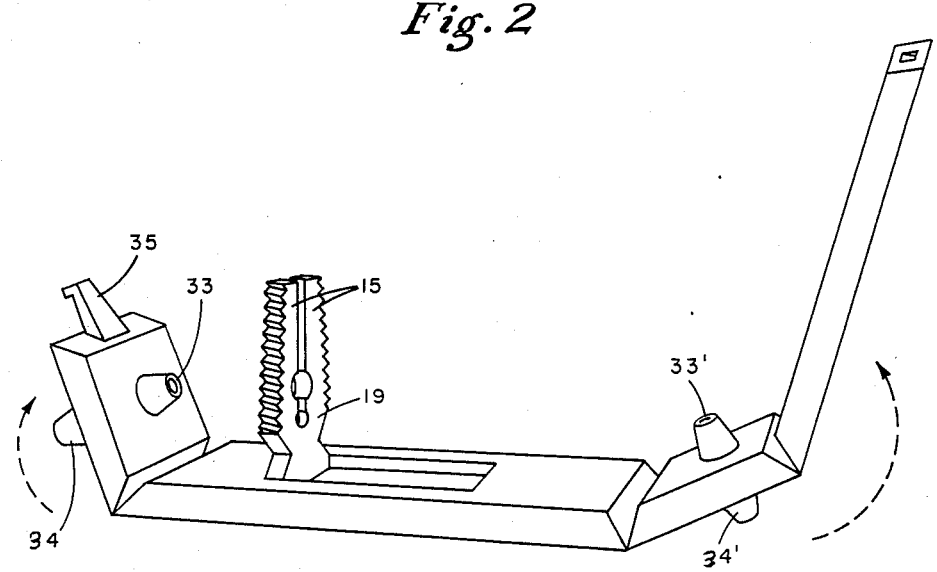
FIG. 4 shows the manner of folding the cassette body to assemble the unit.

These features are also shown in FIG. 4, in which the dashed-line arrows indicate the direction of folding for assembly of the cassette from a preformed sheet. When so folded the flow tube nipples 33, 33' lie on a common line passing between the arms 15 of fork as shown. Complete assembly of the device further includes installation of the flow tube 21 shown in FIG. 2 along the line in that position preferably before fully folding the cassette housing closed. When fully folded, latch 35 protrudes through hole 36 in the top face of the housing securing the housing closed.

Figure 5:
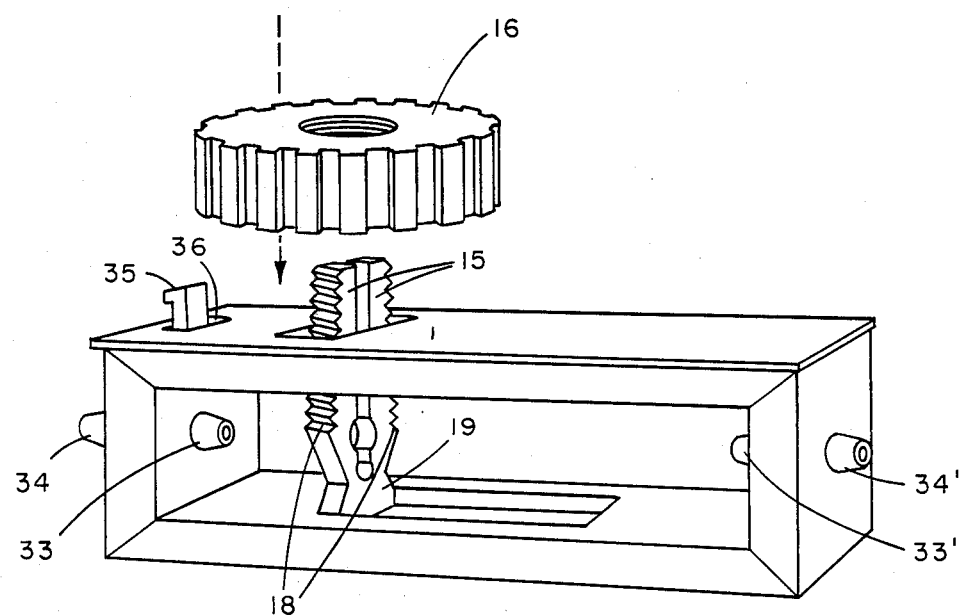
FIG. 5 shows the assembled cassette with adjusting nut.

FIG. 5 shows, in addition to the foregoing features, the adjusting nut 16. The edges of the arms 15 together have the profile of a truncated cone of very small taper and are threaded, as shown, with external threads 18. The threads 18 mate with corresponding threads in the interior of the nut 16, so that by turning the nut so as to advance it toward the base of fork 19 the arms 15 are moved closer together. It will be seen that the actual degree of clamping motion will be a function of the angular taper of the nut, the thread pitch, and the relative point along the clamp arms where the tube crosses. Because the contribution of each of these factors is a fractional factor, it is possible to use a moderate thread pitch and taper slope yet still attain precise control. Such an arrangement allows very fine adjustment of the clamp, reducing the risk of over- and under-clamping which as noted above would lead to an unstable flow rate over an extended period as the tubing wall undergoes deconstriction and cold flow. In actual use the foregoing clamping device results in such ease of control that only very small adjustments to flow are required and the effects of cold flow, and of imperfect tubing memory when overshooting the correct adjustment, are minimal.

One preferred embodiment of the fork member has been found to greatly enhance stability of flow and ease of adjustment. FIG. 6A shows the preferred embodiment of fork member 19, in which the arms 15 are tapered and threaded as previously indicated. A small hole or transverse groove 61 is formed at the base of the channel between the two arms 15, so that the arms are of lesser cross-sectional area adjacent to hole 61, thereby promoting greater flexibility of the arms and a more uniform bending along their length when the adjusting nut 16 is turned. A second hole 62, formed of two opposing indentations in the respective arms 15, is located at the height corresponding to the line determined by the flow tube nipples 33, 33'. One such indentation 63 in an arm 15 is shown in detail in FIG. 6B. The flow tube 21 passes between the two indentations and preferably is cemented to the faces 64 thereof. The arms 15 possess a natural resilience so that when cemented in this manner to the flow tube there is imparted an immediate restoring force on the deformed flow tube walls upon loosening the adjusting nut 16. This restoring force compensates for the imperfect "memory" of the tubing wall, and indeed it operates instantly, greatly expediting the process of setting the flow rate of the clamp.

As noted above the slope of the taper of the arms and the thread pitch each allow the mechanism disclosed to attain a high ratio of angular motion of the adjusting nut to actual clamp action against the tube. This ratio may be further enhanced by the choice of location of the collet element along the length of the clamp arms, with a proportionately lesser constriction occurring as the collet is placed further from the nut end of the arms. However creation of too great a turning to clamping ratio in this manner can render the device more difficult for a human user to control, because many turns of the nut would be required to first set the device at the approximately correct flow rate and the user might indiscriminately overclamp the tube. Accordingly in a preferred embodiment of the collet design, the collet opening is placed approximately halfway along the length of the arms. This provides both a quick commencement of clamping action and a relatively uniform and perceptible rate of constriction upon turning of the nut, allowing highly dependable control.

One immediate advantage provided by the high turning to clamping ratio is that a clamp with such a broad and smooth response pattern may be dependably operated by an automatic rate monitoring device of simple design and calibration. Such an automatic monitoring device may employ a sequence of automatically mediated adjust-and-compare operations to achieve the desired flow rate. In a preferred embodiment, adjustment is accomplished by use of a mating drive gear for meshing with the nut, as shown in FIG. 2; however the nut and control drive may be designed using some alternative mechanical system, e.g. a ratchet and pawl system, to impart the desired control increments of clamp nut rotation. In such a control module drive system the use of 45–60 gear teeth 17 (or alternatively ratchet teeth) would allow stepped control rotations of 6°–8°. While such minor adjustments could be performed by human attendants, their effects could not be readily observed over short time intervals, and a human monitor would thus generally make larger adjustments, requiring subsequent corrections as noted previously. It is not difficult however to design a control mechanism, such as disclosed in my U.S. patent application Ser. No. 254,304 to both perform such minor adjustments and to automatically correct the flow based on long-period observations of the effects of the adjustments. The present clamping device thus lends itself readily to operation by a human attendant or to automatic control via a drop-counting, weight monitoring or other control device, with corresponding improvements in each mode of use.

It will now be clear that the taper and thread arrangement imparts a highly accurate degree of controllable clamping motion to the clamping arms, so that the precise contour of the clamp face portion of the arms will not in general be critical to attainment of a broad and uniform flow restricting action, and many of the contours for the portion of the arm surface which bears against the tubing known in the art will be serviceable for use in the tube-contacting faces of the clamp of the present invention.

Furthermore the flow control device of the present inventory may be embodied in forms not having its distinctive housing.

Accordingly while the invention has been described with particular reference to specific embodiments thereof, it will be understood that it may be embodied in a variety of forms diverse from those shown and described without departing from the spirit and scope of the invention as defined by the following claims.

It will be further appreciated that although the invention has been described as having arms with a tapered threaded end which is engaged by a mating nut, the invention includes tapered threaded arms engaged by a straight threaded nut, or straight threaded arms engaged by a tapered threaded nut. That is, it is not essential that that both the nut and the arms be tapered, or of matching tapers, but only that one of them be tapered. It is also possible to use arms of varying taper with a straight nut, so as to achieve a perceptible stiffening of the action, or a perceptibly different rate of attack.

What is claimed is:

1. A valve for controlling the flow of fluid, such valve comprising:
   a sheet of material having an inlet nipple and an outlet nipple integrally formed therein for receiving the ends of sections of a flow tube;
   flow means, including an elastic tube, for permitting flow of fluid through the inlet nipple in the sheet and then through the outlet nipple in the sheet;
   compression means, mounted on the sheet at the base thereof, for compressing the elastic tube to a desired extent and thus controlling fluid flow through the flow means, the compression means including mating threaded members;
   an advanceable nut with a bore therethrough; and
   a plurality of coplanar, spaced apart arms in hinged connection at their base, the arms having a space for passage of the elastic tube transversely therebetween, and together having an external profile for mating with the nut so that advancement of the nut compresses the arms to adjust the spacing therebetween.

2. A valve according to claim 1, wherein a pair of the arms have free ends distal from their base and contain opposing indentations defining a collet disposed at a distance away from the free ends of the arms for passage of the elastic tube therethrough.

3. A valve according to claim 2, wherein the opposing indentations are each substantially hemi-cylindrical in shape so as to form a substantially cylindrical passage between the arms.

4. A valve according to claim 1 wherein the valve is adapted to removably mount on a separate control module, and wherein the periphery of the nut is adapted to engage a movable drive member of said control module.

5. A valve according to claim 4 wherein the periphery of the nut is toothed for engagement with a drive gear or pawl of the control module.

6. A flow control system comprising:
   a case having an inlet and outlet port;
   a tube, of which at least a portion is located within the case, connecting the inlet to the outlet port;
   a pair of coplanar, spaced apart arms having a central longitudinal axis substantially perpendicular to the case, first and second ends, and interior and exterior faces, the first ends being attached to the case, the arms being so oriented that the tube passes transversely therebetween proximate to a tube-contact surface on the interior face of each arm, and the exterior face of each arm having an adjustment contact surface; and
   adjustable spacing means movably mounted with respect to the arms and actuatable by controlled movement along the longitudinal axis of the arms, for causing adjustable compression of the tube by simultaneously bearing against the adjustment contact surfaces of both arms so as to move one toward the other and thereby to compress the tube.

7. A flow control system according to claim 6, wherein the tube contact surface on each arm includes an indentation disposed at a distance away from the second end toward the first end thereof, the indentations being substantially in registry so as to form a collet in said arms for passage of the tube therethrough.

8. A flow control system according to claim 7, wherein the indentations are substantially semicircular opposing indentations.

9. A flow control system according to claim 6, wherein the second ends of the arms together have an external profile and wherein the adjustable spacing means includes a threaded cylindrical member with a bore forming an interior surface for bearing against the adjustment contact surface of each arm, the axis of the bore being generally coincident with the longitudinal axis.

10. A flow control system according to claim 9, wherein at least one of the bore and the external profile is tapered.

11. A flow control system according to claim 10, wherein both the external profile and the cylindrical bore are threaded, and the cylindrical member is movably mounted by threaded engagement with the external profile.

12. A flow control system according to claim 6, wherein the adjustable spacing means includes coupling means for engaging with a movable drive member of a drive unit for actuating the adjustable spacing means along the longitudinal axis of the arms, and wherein the case includes mounting means for removably mounting the flow control system to the drive unit in such manner as to engage the coupling means with the drive member.

13. A flow control system according to claim 12, wherein the coupling means and the drive member are mating gears.

14. A flow control system according to claim 13, wherein the mounting means includes a plurality of coplanar flanges and the drive unit has a plurality of parallel channels, so that by sliding the flanges along the channels, the case is removably mounted to the drive unit and the gear of the adjustment means is engaged with the drive unit gear.

15. A valve for controlling the flow of fluid, such valve comprising:
   a sheet of material, having inside and outside surfaces, the sheet of material being folded along two approximately parallel folding axes so as to have first and second walls, the inside surface of the first and second walls forming opposing faces, the first and second walls linked between the folding axes by a third wall, each of such first and second opposing walls having integral nipple ports therein;
   a flow tube extending from a nipple port of the first wall to a nipple port of the second wall; and
   compression means, mounted on the sheet, for compressing the flow tube to a desired extent and thus controlling fluid flow through the flow tube, the compression means including mating threaded members, the mating threaded members further including:

a nut with a bore therethrough; and a pair of arms having a space for passage of the elastic tube transversely therebetween, and together having an external profile at one end for mating with the nut so that advancement of the nut compresses the arms to adjust the spacing therebetween, such arms being mounted at their base to the sheet.

16. A valve according to claim 15, wherein the pair of arms contain s opposing indentations disposed proximate to their base defining a collet for passage of the elastic tube therethrough.

17. A valve according to claim 16, wherein the opposing indentations are each substantially semicircular in shape so as to form a passage between the arms with a substantially circular cross-section, the diameter of which is adjustable by operation of the compression means.

18. A valve according to claim 15 wherein the valve is adapted to removably mount on a separate control module and herein the nut is adapted to be rotated by a gear or pawl drive member of the control module.

19. A valve according to claim 15, wherein the arms are integrally formed with the third wall and foldably attached thereto at the ends thereof opposite those mating with the nut.

20. A valve according to claim 15, wherein at least one of the bore and the external profile is tapered.

* * * * *